US006200366B1

(12) United States Patent
Bülow et al.

(10) Patent No.: US 6,200,366 B1
(45) Date of Patent: Mar. 13, 2001

(54) SEPARATION OF ALKENES AND ALKANES

(75) Inventors: Martin Bülow, Basking Ridge; Chang Jie Guo, Bridgewater; Dongmin Shen, Berkeley Heights; Frank R. Fitch, Bedminster; Arthur I. Shirley, Piscataway; Virginia A. Malik, Linden, all of NJ (US)

(73) Assignee: The BOC Group, Inc., Murray Hill, NJ (US)

( * ) Notice: Subject to any disclaimer, the term of this patent is extended or adjusted under 35 U.S.C. 154(b) by 0 days.

(21) Appl. No.: 09/388,105

(22) Filed: Sep. 1, 1999

Related U.S. Application Data

(63) Continuation-in-part of application No. 09/040,574, filed on Mar. 18, 1998, now abandoned.

(51) Int. Cl.$^7$ ................................................. B01D 53/047
(52) U.S. Cl. ............................... 95/101; 95/102; 95/103; 95/105; 95/144; 95/902
(58) Field of Search .................... 95/96–98, 100–105, 95/143, 144, 902; 208/310 Z; 585/654, 655, 809, 820, 829

(56) References Cited

U.S. PATENT DOCUMENTS

| 2,963,519 | 12/1960 | Kasperik et al. ................... 95/144 X |
| 3,723,561 | 3/1973 | Priegnitz ............................. 95/144 X |
| 3,785,122 | 1/1974 | Yatsurugi et al. .................. 95/144 X |
| 3,982,912 | 9/1976 | Yatsurugi et al. .................. 95/144 X |
| 4,137,054 | 1/1979 | Miyake et al. ..................... 95/902 X |
| 4,453,952 | 6/1984 | Izumi et al. ....................... 95/902 X |
| 4,461,631 | 7/1984 | Itabashi et al. ................... 95/902 X |
| 4,498,910 | 2/1985 | Benkmann .......................... 95/144 X |
| 4,554,141 | 11/1985 | Scull et al. ............................. 95/144 |
| 4,917,711 | 4/1990 | Xie et al. .......................... 423/247 X |
| 5,206,004 | 4/1993 | Park .................................... 95/144 X |
| 5,245,099 | 9/1993 | Mitariten ............................ 95/144 X |
| 5,365,011 | 11/1994 | Ramachandran et al. ........... 585/829 |
| 5,507,857 | 4/1996 | Kumar et al. ...................... 95/144 X |
| 5,744,687 | 4/1998 | Ramachandran et al. ......... 95/902 X |

FOREIGN PATENT DOCUMENTS 150 885   9/1981   (DE) .

OTHER PUBLICATIONS

Zeolite Molecular Sieves: Structure, Chemistry, and Use, Donald W. Breck, Krieger Publishing Company, Malabar, Florida (1984), pp. 608–650.

Y. T. Yeh and R. T. Yang, "Diffusion in Zeolites Containing Mixed Cations", AIChE Journal, Oct. 1989, vol. 35, No. 10, pp. 1659–1666.

"Modification of the sorption properties of Linde sieve A by cation exchange and pre–sorption of ammonia", T. Berry, Chemistry Dept., Imperial College of Science and Technology, London, S.W.7, Oct, 1996, pp. 111, 112, 114, and 143.

Journal of the American Chemical Society, vol. 78, No. 23, Dec. 8, 1956, by D. W. Breck, W. G. Eversole, R. M. Milton, T. B. Reed and T. L. Thomas–Crystalline Zeolites. I. The Properties of a New Synthetic Zeolite, Type A, pp. 5963–5977.

*Primary Examiner*—Robert H. Spitzer
(74) *Attorney, Agent, or Firm*—Philip H. Von Neida; Salvatore P. Pace

(57) ABSTRACT

Ethene is separated from a gas mixture containing ethane by a pressure swing adsorption process carried out at a temperature in the range of about 50 to about 200° C., wherein the adsorption step of the process is conducted by passing the gas mixture through an adsorption zone containing type A zeolite whose exchangeable cations are preferably made up of at least about 60 but not more than 75% sodium ions and more than 25 and up to about 40 percent potassium ions.

19 Claims, No Drawings

SEPARATION OF ALKENES AND ALKANES

RELATED CASE

This is a continuation-in-part of application Ser. No. 09/040,574, filed Mar. 18, 1998 now abandoned.

FIELD OF THE INVENTION

This invention relates to the separation of hydrocarbon gases, and more particularly to the separation of gaseous alkenes from alkanes by adsorption. Specifically, the invention relates to the separation of ethene from ethane by pressure swing adsorption (PSA) using a modified type A zeolite adsorbent.

BACKGROUND OF THE INVENTION

It is known to separate alkenes (e.g. propene) from alkanes (e.g. propane) by distillation. The propene-propane mixture is fed into a $C_3$-splitter, which typically is a 2-column distillation system. The second column is substantially equal in size to the first column. The first column separates a substantial portion of the propane to produce a chemical or refinery grade propene of at least 90 volume percent purity, typically about 96 volume percent. The second column improves the purity level to 99+ volume percent to obtain polymer grade propene. The separation of propene from propane by distillation is both difficult and costly because the process requires two large columns and is very energy intensive.

It is also known to separate alkenes from alkanes by adsorption. U.S. Pat. No. 4,917,711 describes the adsorption of an alkene from a mixture containing the alkene and an alkane using an adsorbent comprising a copper compound and a high surface area support such as silica gel or zeolite molecular sieves, such as 4A zeolite, 5A zeolite, type X zeolite or type Y zeolite.

East German Patent No. 150885 describes the separation of alkenes from alkanes using 4A zeolite which has some of its exchangeable cations replaced by calcium or magnesium ions.

U.S. Pat. No. 5,365,011 describes the separation of alkenes having 2 to 6 carbon atoms from alkanes having 2 to 6 carbon atoms by pressure swing adsorption at temperatures in the range of about 50 to about 200° C. using 4A zeolite. The 4A zeolite may have up to 25% of its exchangeable sodium ions replaced by other ions, including potassium ions, calcium ions, strontium ions, etc., provided that the presence of the other ions does not cause the 4A character of the adsorbent to change.

Breck et al, "The Properties of a New Synthetic Zeolite, Type A", Journal of the American Chemical Society, Vol. 78, Number 23, 1956, pp. 5963–5977, describes the adsorption of various hydrocarbons using partially potassium-exchanged type 4A zeolite.

Because of the importance of adsorption as a method of separating alkenes from alkanes, adsorbents having enhanced alkene—alkane separation ability are continuously sought. This invention provides new adsorbents which can efficiently and effectively separate selected alkenes, particularly ethene from selected alkanes, particularly ethane.

SUMMARY OF THE INVENTION

According to a broad embodiment, the invention is a method of separating an alkene selected from ethene, propene, normal butenes or mixtures of these from a gas mixture comprising said alkene and an alkane selected from ethane, propane, normal or branched chain butanes and mixtures of these by a pressure swing adsorption process comprising the steps:

(a) passing the gas mixture through at least one adsorption zone containing type A zeolite having, as its exchangeable cations, about 50 to about 77% sodium ions, about 23 to about 40% potassium ions and about 0 to about 10% other ions selected from Group IA ions other than sodium and potassium, Group IB, Group IIA ions, Group IIIA ions, Group IIIB ions, lanthanide series ions and mixtures of these, thereby adsorbing at least part of said alkene from said gas mixture and producing an alkene-depleted gas; and (b) regenerating the zeolite, thereby producing an alkene-enriched gas.

In a preferred aspect of the broad embodiment, the adsorption step, i.e., step (a), is carried out at a temperature of at least 50° C. In a more preferred aspect, step (a) is carried out at a temperature in the range of about 50 to about 200° C., and in a most preferred aspect of this embodiment, step (a) is carried out at a temperature in the range of about 70 to about 160° C.

In another preferred aspect of the broad embodiment, step (a) is carried out at a pressure in the range of about 1 to about 120 bara, and step (b) is carried out at a pressure in the range of about 0.15 to about 5 bara. In a more preferred aspect, step (a) is carried out at a pressure in the range of about 1 to about 25 bara and step (b) is carried out at a pressure in the range of about 0.2 to about 2 bara.

The method of the invention is particularly useful for the separation of the alkenes from alkanes when the alkene and the alkane being separated contain the same number of carbon atoms.

The method of the invention is especially useful for separating ethene from gas mixtures containing alkanes, especially gas mixtures containing ethane, and it can be effectively used to separate ethene from a gas mixture when the gas mixture contains only ethene and ethane.

In another preferred aspect of the broad embodiment, step (a) comprises passing the gas mixture through type A zeolite whose exchangeable cations comprise more than 25% potassium ions.

In another preferred aspect of the broad embodiment, step (a) comprises passing the gas mixture through type A zeolite having as its exchangeable cations, about 55 to about 73% sodium ions, about 27 to about 40% potassium ions and about 0 to about 5% ions selected from said residual ions, and in a most preferred aspect of this preferred embodiment, step (a) comprises passing the gas mixture through type A zeolite whose exchangeable cations consist substantially of sodium and potassium ions. More preferably the exchangeable cations of said type A zeolite comprise at least about 30% potassium ions, and most preferably they comprise about 30 to about 35% potassium ions.

In another embodiment of the invention, the adsorbent is at least partly regenerated by depressurizing and preferably evacuating the adsorption zone. In this embodiment, or in an independent embodiment, the adsorbent can be at least partly regenerated by purging the adsorption zone with alkene-depleted gas.

In another embodiment, the adsorption zone is purged with alkene-enriched gas prior to step (b).

In another embodiment, step (b) is at least partly carried out by purging the adsorption zone with alkene-depleted gas.

Yet another embodiment comprises purging the adsorption zone with alkene-enriched gas prior to step (b).

Another embodiment comprises at least partly repressurizing the adsorption zone with alkene-depleted gas after step (b).

DETAILED DESCRIPTION OF THE INVENTION

The invention is useful for the separation of gaseous alkenes from gaseous alkanes. The separation is effected by PSA using an adsorbent which more readily adsorbs alkenes than alkanes at the adsorption temperatures employed. Alkenes which can be separated by the process of the invention are the normal alkenes having 2 to 4 carbon atoms, which include ethene, propene, butene-1 and butene-2. In a preferred embodiment, the process of the invention is applied to the separation of ethene from alkanes having 2 to 4 carbon atoms. The most beneficial application of the invention is the separation of ethene from ethane.

The process of the invention can be carried out in a system comprising a single adsorption unit or a battery of adsorption units operated in phase, or a plurality of adsorption units or batteries of adsorption units operated out of phase, whichever is desired. When a system comprising a single adsorption unit or a battery of units all of which are operated in phase is used, the adsorption step must be periodically stopped to permit regeneration of the adsorbent bed(s), whereas when a plurality of adsorption units are employed in parallel and operated out of phase, one or more units can be in adsorption service adsorbing the desired gas component, while one or more other units are undergoing regeneration to desorb and collect the adsorbed gas component. Operation of the adsorption systems of the invention is cyclical. In the preferred adsorption process, cycles are repeatedly carried out in a manner such that production of the desired product gas is substantially continuous. In preferred embodiments of the invention, the process is carried out in a system comprising multivessel adsorption systems with the vessels arranged in parallel and operated out of phase, such that one vessel is in the adsorption phase while another is in the adsorbent regeneration phase, with each vessel being packed with the novel adsorbent of the invention.

The steps of the PSA process used in carrying out the alkene-alkane separation are not critical to the invention. In general, the adsorption cycle includes, as basic steps, an adsorption vessel pressurization step, a production (adsorption) step and an adsorbent regeneration step. During the vessel pressurization step, the pressure in the adsorption vessel in which the adsorption process is carried out is raised to the desired adsorption pressure. During the production step, a gaseous alkene- and alkane-containing feed is passed cocurrently through the adsorption vessel (in the direction from the feed inlet end towards the nonadsorbed product outlet) at the desired adsorption pressure. As the feed gas passes through the adsorption vessel, an alkene-enriched component is adsorbed and an alkene-depleted nonadsorbed gas fraction passes out of the adsorption vessel. The bed regeneration step is carried out by countercurrently (in the direction opposite the cocurrent direction) reducing the pressure in the adsorption vessel and/or evacuating the vessel with a vacuum pump or other evacuation means, thereby desorbing the alkene-enriched product gas from the vessel. The PSA cycle used in the invention may include steps other than the basic steps described above. For example, the cycle may include one or more bed equalization steps, a nonadsorbed product backfill step, a countercurrent nonadsorbed product purge step and a cocurrent desorbed product gas purge step at or below the desired adsorption pressure. The cocurrent purge generally precedes the evacuation step, and is generally carried out before depressurizing the adsorption vessel, although it can be carried out after any cocurrent depressurization steps, e. g. equalization steps. Countercurrent purge is generally carried out during or after countercurrent evacuation of the adsorption vessel. The sequential order and duration of the various steps are not critical, and these may be varied, as desired.

The adsorbent used in the invention is sodium- and potassium-exchanged type A zeolite whose exchangeable cation sites are predominantly occupied by sodium ions. The percentage of exchangeable sites occupied by sodium ions is not greater than about 77%, is preferably less than about 75%, is more preferably not greater than about 73% and is most preferably not greater than about 70%. On the lower end, the percentage of exchangeable sites occupied by sodium ions is generally at least about 50% and is preferably at least about 60% and is more preferably at least about 65%. Conversely, the percentage of exchangeable sites occupied by potassium ions is at least about 23%, is preferably greater than about 25%, is more preferably at least about 27% and is most preferably at least about 30%. On the upper end, the percentage of exchangeable sites occupied by potassium ions is generally not greater than about 40%, and is preferably not greater than about 35%. The zeolite can also have about 0 to about 10% of its exchangeable cation sites occupied by ions other than sodium and potassium ions. When ions other than sodium and potassium ions are present, such other ions preferably do not occupy more than about 5% of the total exchangeable cation sites. Such other ions include Group IA ions other than sodium and potassium, e. g. lithium ions, Group IB ions, e. g. copper I ions, silver I ions, etc., Group IIA ions, e. g. calcium ions, magnesium ions, strontium ions, etc., Group IIIA ions, e. g. aluminum ions, Group IIIB ions, e. g. gallium ions, and ions of the lanthanide series. Preferred adsorbents are type A zeolites whose exchangeable cation sites are occupied substantially by sodium ions and potassium ions. Preferred type A zeolites have substantially only sodium and potassium ions as exchangeable cations, and about 60 to less than 75% of their exchangeable cation sites are occupied by sodium ions and at least about 25 to about 40% of its sites are occupied by potassium ions, and most preferred adsorbents are type A zeolites having substantially only sodium and potassium ions as exchangeable cations and about 65 to about 70% of whose sites are occupied by sodium ions and about 30 to about 35% of whose sites are occupied by potassium ions.

The temperature at which the adsorption step of the PSA process is carried out depends upon a number of factors, such as the particular alkene and alkane being separated, the particular adsorbent being used and the pressure at which the adsorption step is carried out. In general, the adsorption step is carried out at a minimum temperature of about 50° C., and it is preferably carried out at a minimum temperature of about 70° C. The upper temperature at which the adsorption step of the process is carried out is a matter of choice. In general, the adsorption step can be carried out at a temperature below the temperature at which the alkene being separated undergoes chemical reaction, e. g. oligomerization or polymerization. In general, the adsorption step of the process can be carried out at temperatures up to about 200° C., but in preferred embodiments the upper adsorption temperature does not exceed about 175° C., and in most preferred embodiments, it does not exceed about 160° C.

The pressures at which the adsorption and adsorbent regeneration steps are carried out are likewise a matter of choice, and in general, these steps can be carried out at any of the usual pressures employed for gas PSA processes. The pressure at which the adsorption step is carried out is determined by economics. Typically, the adsorption step is carried out at pressures in the range of about 0.5 to about 50 bara (bar absolute), and this step is preferably carried out at pressures in the range of about 1 to about 25 bara; and typically, the adsorbent regeneration step is carried out at pressures in the range of about 1.5 to about 5 bara and this step is preferably carried out at pressures in the range of about 0.2 to about 2 bara.

It will be appreciated that it is within the scope of the present invention to utilize conventional equipment to monitor and automatically regulate the flow of gases within the system so that it can be fully automated to run continuously in an efficient manner.

The invention is further illustrated by the following examples in which, unless otherwise indicated, parts, percentages and ratios are on a volume basis.

The examples were carried out in a laboratory piezometric sorption apparatus comprising an adsorbent-containing sorption cell and a gas-dosing volume that are linked by an isolation valve, at least one high accuracy pressure transducer which measures the pressure change of adsorbates as a function of time, and temperature and vacuum control units for the sorption system.

EXAMPLES 1–5

Adsorbent samples being tested (about 0.5–2 g) are placed in the sorption cell and activated in-situ at 400° C. under a vacuum of less than $10^{-4}$ torr for 3 hours prior to adsorption measurements. The adsorption measurement procedure comprises the following steps: (1) the pure adsorbate is admitted into the gas-dosing volume; (2) the isolation valve is then rapidly opened, thereby allowing the adsorbate to enter the adsorption cell; (3) the pressure change occurring in the adsorption system is followed by a pressure sensor and recorded by means of a data acquisition system into a computer file. After the adsorbate/adsorbent system reaches a new equilibrium, steps (1)–(3) are repeated for the next data point. Adsorption equilibrium capacities for ethene and ethane, measured at 120° C. and 700 torr, and adsorption selectivities based on the pure component equilibrium capacity data are given in the Table. Adsorbent A is zeolite A substantially all of whose exchangeable cations are sodium ions; adsorbent B is zeolite A having as exchangeable cations 79.4% sodium ions and 20.6% potassium ions; adsorbent C is zeolite A having as exchangeable cations 76.3% sodium ions and 23.7% potassium ions; adsorbent D is zeolite A having as exchangeable cations 71.5% sodium ions and 28.5% potassium ions; and adsorbent E is zeolite A having as exchangeable cations 68.4% sodium ions and 31.6% potassium ions.

TABLE

| | | Adsorption Capacity, mol/kg | | |
|---|---|---|---|---|
| Example | Adsorbent | Ethene | Ethane | Selectivity α(ethene/ethane) |
| 1 | A | 6.0 | 2.4 | 2.5 |
| 2 | B | 3.3 | 2.0 | 1.7 |
| 3 | C | 3.2 | 1.6 | 2.0 |
| 4 | D | 3.0 | 1.3 | 2.3 |
| 5 | E | 2.5 | 0.3 | 8.3 |

A comparison of the results of the examples illustrates that equilibrium selectivity for ethene over ethane initially decreases as the percentage of potassium ions substituted for sodium ions on zeolite A increases from zero to 20.6 percent. The selectivity passes through a minimum and unexpectedly shows an increase as the potassium exchange concentration of the adsorbent passes through 23.7 percent. The selectivity continues to increase thereafter and shows a very substantial increase at an exchange concentration of 31.6 percent potassium.

Although the invention has been described with particular reference to specific embodiments and to specific experiments, these features are merely exemplary of the invention and variations are contemplated. For example, the duration of the individual steps and the operating conditions may be varied. Also, the adsorption cycle may include other steps. The scope of the invention is limited only by the breadth of the appended claims.

What is claimed is:

1. A method of separating an alkene selected from ethene, propene, normal butenes or mixtures of these from a gas mixture comprising said alkene and an alkane selected from ethane, propane, butanes and mixtures of these by a pressure swing adsorption process comprising the steps:

(a) passing said gas mixture through at least one adsorption zone containing type A zeolite having, as its exchangeable cations, about 55% to about 73% sodium ions, about 27% to about 40% potassium ions and about 0% to about 5% other ions selected from Group IA ions other than sodium and potassium, Group IB, Group IIA ions, Group IIIA ions, Group IIIB ions, lanthanide series ions and mixtures of these, thereby adsorbing at least part of said alkene from said gas mixture and producing an alkene-depleted gas; and (b) regenerating said zeolite, thereby producing an alkene-enriched gas.

2. The method of claim 1, wherein step (a) is carried out at a temperature of at least 50° C.

3. The method of claim 2, wherein step (a) is carried out at a pressure in the range of about 1 to about 120 bara.

4. The method of claim 3, wherein about 30% to about 40% of the exchangeable cations of said type A zeolite are potassium ions.

5. The method of claim 4, wherein step (a) is carried out at a temperature in the range of about 50 to about 200° C.

6. The method of claim 5, wherein step (b) is carried out at a pressure in the range of about 0.15 to about 5 bara.

7. The method of claim 6, wherein said alkene and said alkane contain the same number of carbon atoms.

8. The method of claim 6, wherein said alkene is ethene.

9. The method of claim 8, wherein said alkane is ethane.

10. The method of claim 9, wherein said gas mixture consists substantially of ethene and ethane.

11. The method of claim 8, wherein step (a) is carried out at a temperature in the range of about 70 to about 160° C.

12. The method of claim 11, wherein step (a) is carried out at a pressure in the range of about 1 to about 25 bara and step (b) is carried out at a pressure in the range of about 0.2 to about 2 bara.

13. The method of claim 12, where in the exchangeable cations of said zeolite consist substantially of sodium and potassium ions.

14. The method of claim 13, wherein at least about 30% of the exchangeable cations of said zeolite are potassium ions.

15. The method of claim 14, wherein about 30% to about 35% of the exchangeable cations of said zeolite are potassium ions.

16. The method of claim 1, wherein step (b) is at least partly carried out by depressurizing said adsorption zone.

17. The method of claim 1 or claim 16, wherein step (b) is at least partly carried out by purging said adsorption zone with alkene-depleted gas.

18. The method of claim 1, further comprising purging said adsorption zone with alkene-enriched gas prior to step (b).

19. The method of claim 1, further comprising at least partly repressurizing said adsorption zone with alkene-depleted gas after step (b).

* * * * *